US009861568B2

(12) United States Patent
Kim et al.

(10) Patent No.: US 9,861,568 B2
(45) Date of Patent: Jan. 9, 2018

(54) COMPOSITION FOR IMPROVING SKIN CONDITIONS, CONTAINING CHLOROPHYLL A OR PHEOPHORBIDE A

(71) Applicant: GWANGJU INSTITUTE OF SCIENCE AND TECHNOLOGY, Gwangju (KR)

(72) Inventors: Yong Chul Kim, Gwangju (KR); Jung Hyun Han, Gwangju (KR); Hyun You, Cheongju-si (KR); Min-Jeong Kim, Busan (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 0 days.

(21) Appl. No.: 15/315,936

(22) PCT Filed: Jan. 30, 2015

(86) PCT No.: PCT/KR2015/001024
§ 371 (c)(1),
(2) Date: Feb. 28, 2017

(87) PCT Pub. No.: WO2015/186888
PCT Pub. Date: Dec. 10, 2015

(65) Prior Publication Data
US 2017/0189292 A1    Jul. 6, 2017

(30) Foreign Application Priority Data
Jun. 2, 2014 (KR) .................. 10-2014-0067083

(51) Int. Cl.
*A61K 31/555* (2006.01)
*A61K 31/35* (2006.01)
*A61K 8/58* (2006.01)
*A61K 8/49* (2006.01)
*A61Q 19/08* (2006.01)
*A61K 31/409* (2006.01)
*A61K 9/00* (2006.01)
*A23L 33/105* (2016.01)

(52) U.S. Cl.
CPC .............. *A61K 8/58* (2013.01); *A23L 33/105* (2016.08); *A61K 8/492* (2013.01); *A61K 9/0053* (2013.01); *A61K 31/409* (2013.01); *A61Q 19/08* (2013.01); *A23V 2002/00* (2013.01)

(58) Field of Classification Search
CPC .............................. A61K 31/555; A61K 31/35
USPC ................................................. 514/184, 456
See application file for complete search history.

(56) References Cited

U.S. PATENT DOCUMENTS

2010/0255045 A1   10/2010  Eymard Du Vernet
2013/0274237 A1*  10/2013  Kim ...................... A61K 31/555
                                                            514/184
2015/0133552 A1*   5/2015  Hans ..................... A23C 9/1565
                                                            514/557

FOREIGN PATENT DOCUMENTS

JP      2009-091349 A       4/2009
KR      10-2009-0093448 A   9/2009
KR      10-2014-0047247 A   4/2014
WO      99/26589 A2         6/1999

OTHER PUBLICATIONS

Gail Jenkins, "Molecular mechanisms of skin ageing", Mechanisms of Ageing and Development, 2002, Elsevier Science Ireland Ltd., 123, pp. 801-810.
Hyeon Ho Kim et al., "Augmentation of UV-induced skin wrinkling by infrared irradiation in hairless mice", Mechanisms of Ageing and Development, 2005, Elsevier Ireland Ltd., 126, pp. 1170-1177.
K. Gelse et al., "Collagens—structure, function, and biosynthesis", Advanced Drug Delivery Reviews, 2003, Elsevier B.V., 55, pp. 1531-1546.
Mario G. Ferruzzi et al., "Assessment of Degradation and Intestinal Cell Uptake of Carotenoids and Chlorophyll Derivatives from Spinach Puree Using an In Vitro Digestion and Caco-2 Human Cell Model", American Chemical Society, 2001, J. Agric. Food Chem., vol. 49, No. 4, pp. 2082-2089.
Benoit Schoefs, "Chlorophyll and carotenoid analysis in food products. Properties of the pigments and methods of analysis", Trends in Food Science & Technology, 2002, Elsevier Science Ltd., 13, pp. 361-371.
Romuald Czerpak et al., "Znaczenie terapeutyczne, kosmetyczne i dietetyczne niektórych glonów Therapeutic, Cosmetic and Dietary Significance of Some Algae", Postę py Fitoterapii, 2009, s, pp. 168-174.
Tomoe Negishi et al., "Antigenotoxic activity of natural chlorophylls", Mutation Research, 1997, Elsevier Science B. V. 376, pp. 97-100.
Yoshimasa Nakamura et al., "Identification of Pheophorbide a and Its Related Compounds as Possible Anti-tumor Promoters in the Leaves of Neptunia oleracea", Bioscience, Biotechnology, and Biochemistry, 1996, 60, pp. 1028-1030.
Yoshimasa Nakamura et al., "Inhibitory effect of pheophorbide α, a chlorophyll-related compound, on skin tumor promotion in ICR mouse", Cancer Letters, 1996, Elsevier Science Ireland Ltd., 108, pp. 247-255.
Ulrich Harttig et al., "Chemoprotection by natural chlorophylls in vivo: inhibition of dibenzo[a,l]pyrene—DNA adducts in rainbow trout liver", Carcinogenesis, 1998, Oxford University Press., vol. 19, No. 7, pp. 1323-1326.

(Continued)

Primary Examiner — Raymond J Henley, III
(74) Attorney, Agent, or Firm — Hauptman Ham, LLP

(57) ABSTRACT

The present disclosure provides a composition for improving skin condition comprising chlorophyll a or pheophorbide a as an active ingredient. According to the present disclosure, chlorophyll a or pheophorbide a exhibits an effect of improving skin wrinkles and inflammatory reaction due to ultraviolet lights. The composition of the present disclosure is characterized by oral administration and can be provided as a cosmetic composition, a pharmaceutical composition or a food composition.

9 Claims, 17 Drawing Sheets

(56) References Cited

OTHER PUBLICATIONS

Thomas J. Dougherty et al., "Photodynamic Therapy", Journal of the National Cancer Institute, Jun. 17, 1998, vol. 90, No. 12, pp. 889-905.
Hiroshi Endo et al., "Isolation of 10-Hydroxypheophorbide a as a Photosensitizing Pigment from Alcohol-treated Chlorella Cells", Agricultural and Biological Chemistry,1982, 46, pp. 2183-2193.
Ichiro Fujishima et al., "Photodynamic Therapy Using Pheophorbide a and Nd:YAG Laser", Neural Med Chir (Tokyo), 1991, 31, pp. 257-263.
Eiichi Matuura et al., "Photodynamic Action of Salted Takana or Pheophorbide a in the Salted Takana on Erythrocyte of Rats", 1977, vol. 30, No. 5, pp. 307-311.
James W. Heaton et al., "Chlorophyll degradation in processed foods and senescent plant tissues", Trends in Food Science & Technology, 1996, vol. 7, Total pp. 8-15.
Michael Heinrich et al., "Pheophorbide a from Solanum diflorum Interferes with NF-kB Activation", Georg Thieme Verlag Stuttgart New York, 2001, Planta Med, 67, p. 156.
Appian Subramoniam et al., "Chlorophyll Revisited: Anti-inflammatory Activities of Chlorophyll a and Inhibition of Expression of TNF-α Gene by the Same", Inflammation, 2012, Springer Science+Business Media, LLC, vol. 35, No. 3, pp. 959-966.
MD Nurul Islam et al., "Anti-inflammatory activity of edible brown alga *Saccharina japonica* and its constituents pheophorbide a and pheophytin a in LPS-stimulated RAW 264.7 macrophage cells", Food and Chemical Toxicology, 2013, Elsevier Ltd, 55, pp. 541-548.
Joo Y. Lee et al., "Saturated Fatty Acid Activates but Polyunsaturated Fatty Acid Inhibits Toll-like Receptor 2 Dimerized with Toll-like Receptor 6 or 1", The Journal of Biological Chemistry, 2004, vol. 279, No. 17, pp. 16971-16979.
Donald L. Bissett et al., "An animal model of solar aged skin: Histological, Physical, and Visible Changes in Un-Irradiated Hairless Mouse Skin", Photochemistry and Photobiology, 1987, vol. 46, No. 3, pp. 367-378.
Jong-Seong Ryu et al., "Improving lip wrinkles: lipstick-related image analysis", Skin Research and Technology, 2005, 11, pp. 157-164.
Jean Krutmann et al., "Involvement of Cytokines, DNA Damage, and Reactive Oxygen Intermediates in Ultraviolet Radiation-Induced Modulation of Intercellular Adhesion Molecule-I Expression", The Journal of Investigative Dermatology, 1995, vol. 105, No. 1, pp. S67-S70.
Gary J. Fisher et al., "Pathophysiology of Premature Skin Aging Induced by Ultraviolet Light", The New England Journal of Medicine, 1997, vol. 337, No. 20, pp. 1419-1428.
Young Mee Lee et al., "Heat-induced MMP-1 expression is mediated by TRPV1 through PKCα signaling in HaCaT cells", Journal compilation, 2008, Blackwell Munksgaard, Experimental Dermatology, 17, pp. 864-870.
Ulpu K. Saarialho-Kere et al., "Matrix Metalloproteinase Matrilysin Is Constitutively Expressed in Adult Human Exocrine Epithelium", The Journal of Investigative Dermatology, 1995, The Society for investigative Dermatology, Inc., vol. 105, No. 2, Aug. 1995, pp. 190-196.
C. D. Ropke et al., "Photoprotective effect of Pothomorphe umbellata root extract against ultraviolet radiation induced chronic skin damage in the hairless mouse", Clinical and Experimental Dermatology, 2005, Blackwell Publishing Ltd, 30, pp. 272-276.
Ho-Song Cho et al., "Anti-wrinkling effects of the mixture of vitamin C, vitamin E, pycnogenol and evening primrose oil, and molecular mechanisms on hairless mouse skin caused by chronic ultraviolet B irradiation", Photodermatol Photoimmunol Photomed, 2007, Blackwell Munksgaard, 23, pp. 155-162.
Tong Ho Kang et al., "Effects of red ginseng extract on UVB irradiation-induced skin aging in hairless mice", Journal of Ethnopharmacology, 2009, 123, pp. 446-451.
Ji-Young Bae et al., "Dietary compound ellagic acid alleviates skin wrinkle and inflammation induced by UV-B irradiation", 2010, Experimental Dermatology, 19, pp. 182-190.
Praveen K. Vayalil et al., "Green Tea Polyphenols Prevent Ultraviolet Light-Induced Oxidative Damage and Matrix Metalloproteinases Expression in Mouse Skin", J Invest Dermatol, 2004, The Society for Investigative Dermatology, Inc., 122, pp. 1480-1487.
Mario G. Ferruzzi et al., "Digestion, absorption, and cancer preventative activity of dietary chlorophyll derivatives", Nutrition Research, 2007, 27, pp. 1-12.
Visalini Muthusamy et al., "The UV response of the skin: a review of the MAPK, NFkB and TNFα signal transduction pathways", Arch Dermatol Res, 2010, 302, pp. 5-17.
Mina Yaar et al., "Aging of Skin", Chapter 108, pp. 963-973.
Joydeb Kumar Kundu et al., "Resveratrol inhibits phorbol ester-induced cyclooxygenase-2 expression in mouse skin: MAPKs and AP-1 as potential molecular targets", BioFactors, 2004, 21, pp. 33-39.
Som D.Sharma et al., "Dietary grape seed proanthocyanidins inhibit UVBinduced oxidative stress and activation of mitogenactivated protein kinases and nuclear factor-KB signaling in in vivo SKH-1 hairless mice", Molecular Cancer Therapeutics, 2007, GSPs Suppress UV-Induced Oxidative Stress, 6, pp. 995-1005.
Guoliang Cui et al., "Berberine Differentially Modulates the Activities of ERK, p38 MAPK, and JNK to Suppress Th17 and Th1 T Cell Differentiation in Type 1 Diabetic Mice", The Journal of Biological Chemistry, 2009, vol. 284, No. 41, pp. 28420-28429.
Li-Chen Wu et al., "Antimelanogenic effect of c-phycocyanin through modulation of tyrosinase expression by upregulation of ERK and downregulation of p38 MAPK signaling pathways", Journal of Biomedical Science, 2011, 18, 74, pp. 1-11.

\* cited by examiner (H&E, 100x)

(Masson-trichrome, 100x)

(H&E, 200x)

(ICAM-1, 200x)

COMPOSITION FOR IMPROVING SKIN CONDITIONS, CONTAINING CHLOROPHYLL A OR PHEOPHORBIDE A

STATEMENT OF GOVERNMENT SUPPORT

The present invention was made with the support of the Ministry of Education, Science, and Technology of the Republic of Korea, under Project No. NN11700, which was conducted under the research project, entitled "General Researcher Support Project (Basic)," within the project named "Study on the Development of Oral FLT3 Inhibitor for the Treatment of Acute Myeloid Leukemia" by the Gwangju Institute of Science and Technology, under the management of the National Research Foundation of Korea, from Nov. 1, 2013 to Oct. 31, 2014.

CROSS REFERENCE TO RELATED APPLICATION

This present application is a national stage filing under 35 U.S.C §371 of PCT application number PCT/KR2015/001024 filed on Jan. 30, 2015 which is based upon and claims the benefit of priority to Korean Patent Application No. 10-2014-0067083 filed on Jun. 2, 2014 in the Korean Intellectual Property Office. The disclosures of the above-listed applications are hereby incorporated by reference herein in their entirety.

CROSS-REFERENCE TO RELATED APPLICATION

The present patent application claims priority to and the benefit of Korean Patent Application No. 10-2014-0067083 filed with the Korean Intellectual Property Office on Jun. 2, 2014, the disclosures of which are incorporated herein by reference.

TECHNICAL FIELD

Field of the Invention

The present disclosure relates to a composition for improving skin condition comprising chlorophyll a or pheophorbide a.

Background Art

Wrinkles, sagging, and relaxation are characteristics of skin aging due to various environmental and genetic factors such as changes in ultraviolet (UV) lights, infrared lights, and hormones [1, 2]. Structural features of aged skin are mainly described by changes in dermis, which include collagen, hyaluronic acid, elastin, fibronectin, proteoglycan, and other extracellular matrix proteins. Among these structural components, type 1 collagen, which is mainly synthesized by fibroblast, is the most abundant protein in a connective tissue of skin and serves to support strength and elasticity to the skin [3].

Continuous exposure to ultraviolet lights is a major cause of premature skin aging and photoaging [23]. Photoaging may be explained by a repeated inflammation process due to ultraviolet lights. Skin inflammation produces a variety of matrix metalloproteinases (MMPs), which break down abnormally extracellular matrix in the dermis and epidermis and cause accumulation of disorganized matrix components [24]. Accumulated skin damage caused by matrix degradation and skin inflammation, etc. causes excessive MMP production, which is related to the formation of wrinkles.

Several compounds and plant extracts have been reported to have anti-inflammatory and anti-wrinkle properties in the skin. It has been discovered that oral dosing of vitamin C, E, pycnogenol and evening primrose oil complexes in animal models (hairless mouse) has the effect of alleviating wrinkles caused by persistent UV exposure [27]. *Ginseng* ingredients, ellagic acids, and green tea polyphenols have also been reported to have the effect of improving UV-induced skin aging [28, 29, 30]. It is described that most polyphenols' wrinkle-improving effects are related to anti-oxidant activity [30], and the functional mechanism that exhibits the wrinkle-improving effects is related to the inhibition of the production of MMPs.

In the present disclosure, the present inventors have found that chlorophyll a and pheophorbide a are effective in relieving skin inflammation and improving wrinkles due to ultraviolet lights. Further, we have found that the pheophorbide a has the effect of inhibiting the production of MMPs induced by ultraviolet lights. These results show that chlorophyll a and pheophorbide a can be used as skin condition improving agents.

Numerous papers and patent documents are referenced and cited throughout this specification. The disclosures of the cited papers and patent documents are incorporated herein by reference in their entirety to better understand the state of the art to which the present disclosure pertains and the content of the present disclosure.

DISCLOSURE

Technical Problem

The present inventors have made efforts to develop a substance capable of effectively improving skin damage due to external stimuli such as ultraviolet lights. As a result, we have found that chlorophyll a and pheophorbide a are very effective for improving skin condition such as skin wrinkles and skin inflammation, and have completed the present disclosure.

Accordingly, an object of the present disclosure is to provide a composition for improving skin condition.

These and other objects and advantages of the present disclosure will become more apparent from the following detailed description of preferred embodiments of the disclosure that is provided in connection with the accompanying drawings.

Technical Solution

According to one aspect of the present disclosure, there is provided a composition for improving skin condition comprising chlorophyll a or pheophorbide a as an active ingredient.

According to another aspect of the present disclosure, there is provided a composition for preventing, improving, or treating skin damage caused by ultraviolet lights, comprising chlorophyll a or pheophorbide a as an active ingredient.

According to still another aspect of the present disclosure, there is provided a composition for preventing or treating sunburn comprising chlorophyll a or pheophorbide a as an active ingredient.

The present inventors have made efforts to develop a substance capable of effectively improving skin damage caused by external stimuli such as ultraviolet lights. As a result, we have found that chlorophyll a and pheophorbide a are very effective for improving skin conditions such as for improving skin wrinkles and for alleviating skin inflammation.

Chlorophyll is the most abundant ingredient in plants, types a and b of the chlorophyll generally existing in the ratio of 3:1 to 3:2 in higher plants. Traditionally, plant chlorophyll has been used for the management of injuries such as wounds, burns and ulcers through an anti-inflammatory effect [4] and has also been used as a health food for health promotion [5]. In addition, a cosmetic composition of plant extracts containing chlorophyll has been used to manage skin damage [6].

Chlorophyll produces a variety of derivatives, including pheophytin, pheophorbide, chlorin, and phytanic acid. Previous researchers have found that chlorophyll derivatives, including chlorophyll, pheophytin and pheophorbide, have potential chemical-cancer preventing functions [7, 8]. In addition, it has been shown that pheophytin, pyropheophytin and pheophorbide derivatives, which are commonly found in canned green vegetables, have potential tumor suppression effects [9,10]. Pheophorbide is also known as a phototoxic substance used in photodynamic therapy for cancer [11]. However, the effects of pheophorbide or chlorophyll on the improvement of skin wrinkles have not yet been fully understood.

As used herein, the term "improvement of skin condition" means improvement of skin wrinkles, alleviation of skin inflammation or prevention of skin aging, but is not limited thereto.

Skin wrinkles are caused by degeneration of collagen fibers and elastic fibers in the dermis due to various factors including sunlight, followed by a reduction in skin moisture, resulting in less elasticity of the skin and then folding of the skin. Among the various factors, ultraviolet light is the main cause.

According to some embodiments of the present disclosure, oral administration of chlorophyll a or pheophorbide a after irradiating ultraviolet lights (UV) on a mouse has an effect of improving wrinkles.

In skin inflammation, immune cell activity plays an important role. Activated immune cells or cytokines produced by immune cells continuously stimulate peripheral assisted cells to induce side effects such as excessive activation of cells or destruction of tissue through cell death, resulting in an inflammatory reaction. In skin inflammation, adhesion molecule plays an important role in binding between keratinocyte, monocyte, and lymphocyte, including intracellular adhesion molecule-1 (ICAM-1), vascular adhesion molecule-1 (VCAM-1), E-selection, and the like. These adhesion molecules infiltrate various immune-related cells into skin tissues, resulting in inflammatory reactions through various interactions between skin cells and immune cells. Therefore, the skin inflammatory reactions can be alleviated by suppressing the expression of these adhesion molecules.

According to certain embodiments of the present disclosure, when chlorophyll a or pheophorbide a was orally administered to a mouse after irradiation with ultraviolet lights (UV), the expression of ICAM-1 decreased and infiltration of inflammatory cells in the dermis decreased. These results indicate that chlorophyll a or pheophorbide a has the effect of alleviating the skin inflammatory reaction caused by ultraviolet lights.

Skin aging can be classified into an intrinsic aging and an extrinsic aging depending on the factors that affect aging. The intrinsic aging is due to the aging of the skin structure and physiological function, regardless of environmental changes, and the extrinsic aging is caused by the skin being continuously exposed to the external environment such as sunlight. In particular, aging by light is called photoaging, and ultraviolet light is a major cause of physiological and morphological changes in skin aging. If a harmful active oxygen generated by ultraviolet lights is not effectively removed by various protective devices in a body, a series of inflammatory reactions occur, resulting in skin damage.

The chlorophyll a or pheophorbide a of the present disclosure exhibits the effect of improving skin wrinkles and skin inflammation due to ultraviolet lights, which means that it has the effect of improving the skin condition due to photoaging amongst the skin aging.

There are three types of ultraviolet lights (UV): UVA (200-280 nm), UVB (280-320 nm) and UVC (320-400 nm). UVC is almost absorbed by ozone layer, and only UVA and UVB reach the surface and affect the skin. Particularly, UVB among the UV lights causes the most serious damage to the skin. UVB reaches to the upper part of the dermis and causes rapid burns or erythema. Further, melanin pigment formation and pigmentation occur when it progresses, causing epithelial cell proliferation, DNA damage and the like, leading to skin wrinkles and skin cancer. It is also known to cause an inflammatory reaction in skin cells.

As described above, chlorophyll a or pheophorbide a of the present disclosure is effective in improving the skin wrinkles and skin inflammation due to ultraviolet lights, and thus can be effectively used for prevention, improvement, or treatment of the skin damage caused by ultraviolet lights.

The main cause of "sunburn" in the present specification is ultraviolet lights. When ultraviolet lights reach the skin, they act directly on the blood vessel walls. Most of them are absorbed by skin cells and stimulated to release histamine, prostaglandin, etc. These inflammatory substances increase the permeability of the vascular walls, causing inflammatory cells to migrate from the blood vessels to the skin tissue. That is, the ultraviolet lights cause an inflammation reaction to the skin, and symptoms such as erythema, hot feeling, pain and swelling appear. Therefore, if inflammatory cells are inhibited from invading the skin tissue in the blood vessels, it is possible to prevent or treat sunburn by suppressing the skin inflammatory reaction.

According to some embodiments of the present disclosure, infiltration of inflammatory cells in the dermis is decreased when chlorophyll a or pheophorbide a is orally administered to mice after irradiation with ultraviolet (UV) light.

According to some embodiments of the present disclosure, the production of MMP-1 and MMP-3 is reduced when treating the pheophorbide a after UV irradiation in human dermal fibroblasts.

Matrix metalloproteinases (MMPs) are zinc-dependent endopeptidases. They are able to degrade all types of extracellular matrix and play an important role in cell proliferation, differentiation, migration, angiogenesis and cell apoptosis. Particularly, ultraviolet lights increase the production of MMPs in the skin, thereby causing a skin aging reaction such as formation of wrinkles by decomposing collagen. That is, inhibiting the production of MMPs in the skin exposed to ultraviolet lights can prevent or treat skin damages caused by ultraviolet lights.

MMP-1 is known to be involved in the degradation of extracellular matrix in the process of disease as well as normal physiological reaction, and particularly acts to decompose collagen types I, II and III.

MMP-3 functions to degrade collagen types II, III, IV, IX and X, proteoglycans, fibronectin, laminin and elastin, and also activates MMPs such as MMP-1, MMP-7 and MMP-9.

Thus, MMP-3 is considered to be the most important factor in reconstitution of skin tissue.

The composition of the present disclosure can be provided as a cosmetic composition for oral skin improvement. The cosmetic composition of the present disclosure contains, as an active ingredient, components commonly used in food compositions or oral medicines in addition to the above-mentioned chlorophyll a or pheophorbide a, and may include conventional auxiliaries such as, for example, antioxidants, stabilizers, solubilizers, vitamins, pigments and flavoring agents, and also include carriers.

Carriers contained in the oral cosmetic composition of the present disclosure are those conventionally used in the formulation thereof, and may include, but are not limited to, lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil. The oral cosmetic composition of the present disclosure may further include a lubricant, a wetting agent, a sweetening agent, a flavoring agent, an emulsifying agent, a suspending agent, a preservative, etc. in addition to the above components.

Further, the composition of the present disclosure may be formulated as a pharmaceutical composition.

According to a preferred embodiment of the present disclosure, the composition of the present disclosure is a pharmaceutical composition, including: (a) a pharmaceutically effective amount of chlorophyll a or pheophorbide a of the present disclosure; and (b) a pharmaceutically acceptable carrier. As used herein, the term "pharmaceutically effective amount" means an amount sufficient to achieve efficacy or activity of chlorophyll a or pheophorbide a.

When the composition of the present disclosure is prepared as a pharmaceutical composition, the pharmaceutical composition of the present disclosure includes a pharmaceutically acceptable carrier. The pharmaceutically acceptable carrier contained in the pharmaceutical composition of the present disclosure are those conventionally used in the formulation thereof, and may include, but are not limited to, lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil. The pharmaceutical composition of the present disclosure may further include a lubricant, a wetting agent, a sweetening agent, a flavoring agent, an emulsifying agent, a suspending agent, a preservative, etc. in addition to the above components. Suitable pharmaceutically acceptable carriers and agents are described in detail in Remington's Pharmaceutical Sciences (19th ed., 1995).

The pharmaceutical composition of the present disclosure can be administered orally.

A suitable dosage of the pharmaceutical composition of the present disclosure may vary depending on such factors as formulation method, administration mode, age, body weight, sex, pathological condition, food, administration time, administration route, excretion rate, and responsiveness.

The pharmaceutical composition of the present disclosure may be formulated into a unit dose form or loaded into a multi-dose container by formulating it using a pharmaceutically acceptable carrier and/or excipient according to methods which can be easily carried out by those having ordinary skill in the art to which the present disclosure belongs. Such formulation may be in the form of solutions, suspensions, syrups, or emulsions in oil or aqueous media, or in the form of extracts, powders, granules, tablets or capsules, and may additionally contain dispersing or stabilizing agents.

In addition, the composition of the present disclosure may be provided as a food composition.

According to a preferred embodiment of the present disclosure, the composition of the present disclosure is a food composition comprising (a) a sitologically effective amount of chlorophyll a or pheophorbide a of the present disclosure; and (b) a sitologically acceptable carrier.

When the composition of the present disclosure is prepared as a food composition, it contains not only chlorophyll a or pheophorbide a as an active ingredient, but also components normally added in the production of food, such as, for example, protein, carbohydrate, fat, nutrients, and seasoning and flavoring agents. Examples of the above-mentioned carbohydrates include monosaccharides such as glucose, fructose, etc.; disaccharides such as maltose, sucrose, oligosaccharides, etc.; and polysaccharides such as dextrin, cyclodextrin, etc., and sugar alcohols such as xylitol, sorbitol, erythritol, etc. As a flavoring agent, natural flavoring agents such as tau martin and *stevia* extract (e.g., rebaudioside A and glycyrrhizin) and synthetic flavoring agents such as saccharin, aspartame, etc. can be used. For example, when the food composition of the present disclosure is prepared as a drink, in addition to *Smilax glabra* extract of the present disclosure, it may further include citric acid, liquid fructose, sugar, glucose, acetic acid, malic acid, fruit juice, mulberry extract, jujube extract, licorice extract, etc.

Advantageous Effects

The features and advantages of the present disclosure are summarized as follows:
(a) The present disclosure provides a composition for improving skin condition comprising chlorophyll a or pheophorbide a as an active ingredient;
(b) According to the present disclosure, chlorophyll a or pheophorbide a exhibits an effect of improving skin wrinkles caused by ultraviolet lights;
(c) According to the present disclosure, chlorophyll a or pheophorbide a exhibits an effect of alleviating an inflammatory reaction caused by ultraviolet lights; and
(d) The composition of the present disclosure is characterized by oral administration and can be provided as a cosmetic composition, a pharmaceutical composition, and a food composition.

DESCRIPTION OF DRAWINGS

FIG. 1*a* is a photograph showing a reduction of wrinkles in a dorsal skin of mice administered with chlorophyll a or pheophorbide a.

FIG. 2*a* is a photograph showing that the infiltration of inflammatory cells was reduced in comparison with a mouse in which only UV was irradiated in the dermis of the mouse administered with pheophorbide a.

FIG. 2b is a photograph showing that the thickness of epidermis was significantly decreased and collagen bundle was thicker in the dermis in a mouse administered with pheophorbide a or chlorophyll a.

FIG. 3a is a photograph showing that the infiltration of inflammatory cells was reduced in comparison with a mouse in which only UV was irradiated in the dermis of the mouse administered with pheophorbide a.

FIG. 4a is a graph showing cell viabilities after irradiating hDF cells with UV and treating various concentrations of pheophorbide a.

FIG. 4b is a photograph showing Western blotting analysis of changes in expression levels of MMP-1, 2 and 3 proteins after irradiating hDF cells with UV and treating various concentrations of pheophorbide a.

FIG. 4c is a graph showing the mRNA expression level of MMP-1 by real-time RT-PCR after irradiating hDF cells with UV and treating various concentrations of pheophorbide a.

FIG. 4d is a graph showing the mRNA expression level of MMP-2 by real-time RT-PCR after irradiating hDF cells with UV and treating various concentrations of pheophorbide a.

FIG. 4e is a graph showing the mRNA expression level of MMP-3 by real-time RT-PCR after irradiating hDF cells with UV and treating various concentrations of pheophorbide a.

FIG. 5a is a photograph showing Western blotting analysis of changes in expression levels of pJNK, JNK, pERK1/2 and ERK1/2 proteins after irradiating hDF cells with UV and treating various concentrations of pheophorbide a.

BEST MODE

Figure 1A:
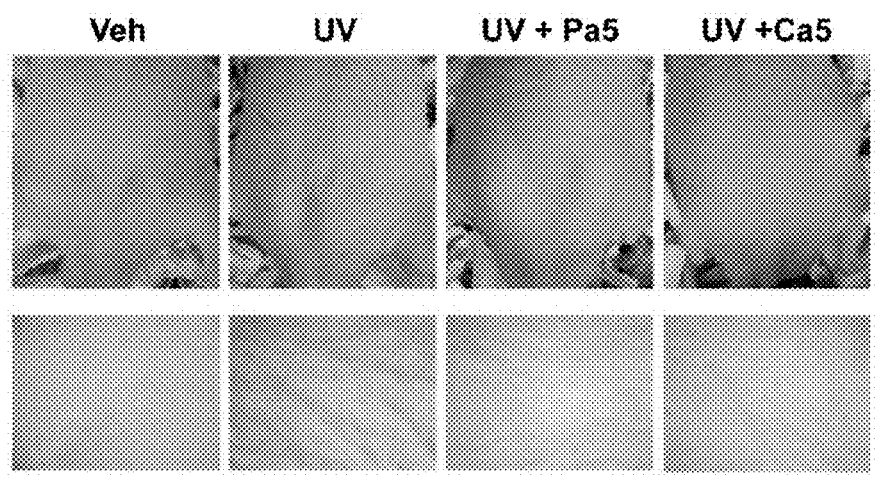
Figure 1B:
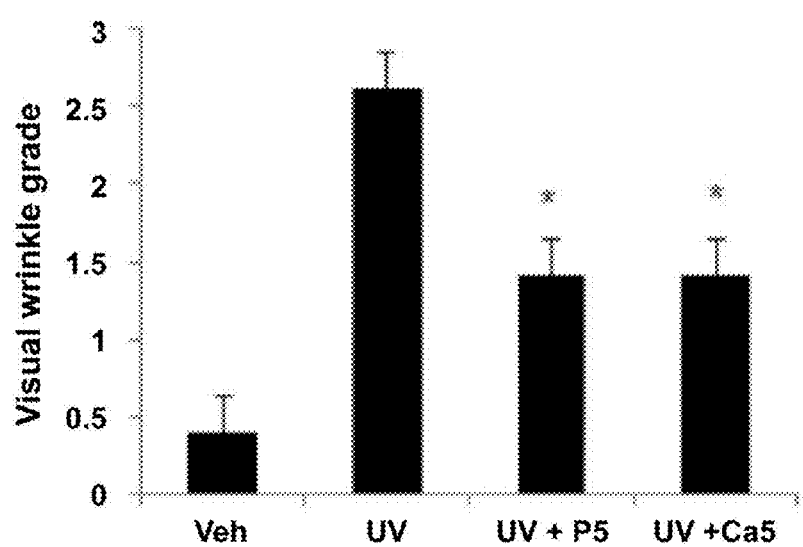
FIG. 1*b* is a graph showing that visual wrinkle grade in the group of mice administered with chlorophyll a or pheophorbide a was significantly decreased compared to the group only irradiated with UV.
Figure 1C:
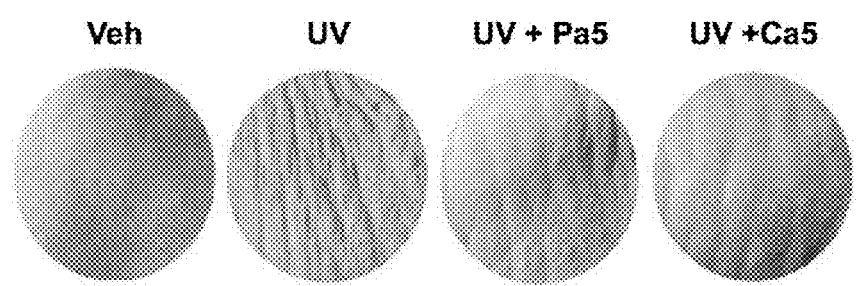
FIG. 1*c* is the wrinkles exhibited by negative replicates in mice.
Figure 1D:
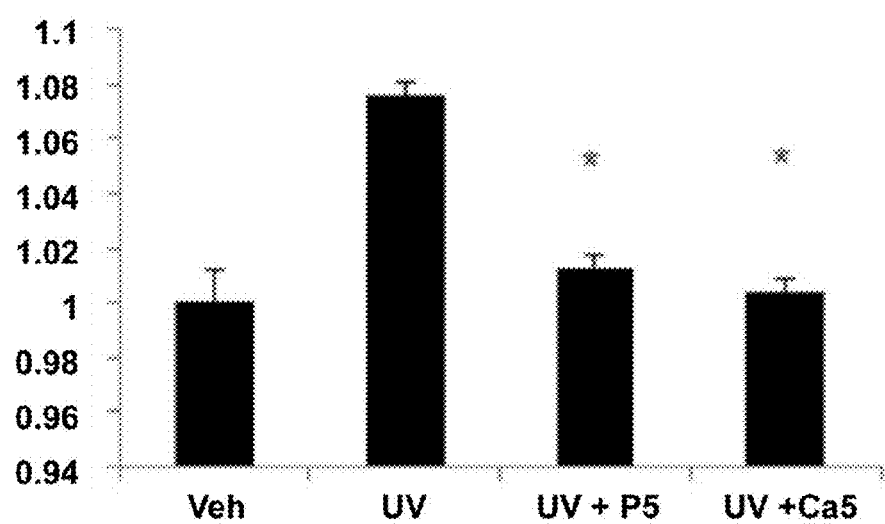
FIG. 1*d* is a diagram of a corrugated region of a dorsal skin using a shadow region.

Hereinafter, the present disclosure will be described in more detail by way of examples.

It is to be understood by those skilled in the art that these examples are only for illustrating the present disclosure in more detail and that the scope of the present disclosure is not limited by these examples in accordance with the gist of the present disclosure.

EXAMPLES

Experimental Materials and Methods

Cell Culture

The primary human dermal fibroblast (hDF) cell line was obtained from Chonnam National University Medical School (Gwangju, Republic of Korea). The cells were cultured at 37° C. and under 5% $CO_2$ using Dulbecco's Modified Eagle's Medium (DMEM, Gibco Laboratories, Grand Island, N.Y., USA) supplemented with 5% fetal bovine serum (Gibco Laboratories, Grand Island, N.Y., USA) and 1% penicillin (100 units/ml)/streptomycin (100 mg/ml).

[UV Irradiation]

Philips TL 20W/12 RS fluorescent sun lamp with emission spectra of 280 nm and 380 nm was used as an UV source. The UV intensity at the skin surface was measured using a UV detector (GUVx-T1xGS5-LA2, Genicom Daejeon, Korea). The UV irradiation intensity was 1.0 mW/cm2 at 30 cm from the UV source. The cells were cultured up to 75-80% of culture dish, washed twice with PBS buffer, and irradiated with UV to treat test materials. Thereafter, the cells were continuously cultured in the absence of light until the next analysis.

In order to irradiate animals with UV, the minimal erythema dose (MED) of the dorsal skin of mice was examined first. Minimal erythema dose means the minimum amount of erythema that can be derived with a clear border after 24 hours of irradiation. The mice were irradiated three times a week for 8 weeks with UV. During the first 3 weeks, the dose was increased by 1 MED (herein, 1 MED=30 mJ/cm2), and then 3 MED was maintained thereafter.

[Cell Viability Assay]

A water soluble tetrazolium test method was used for cell viability analysis. Quantification of living cells was performed using a 30 Ez-cytox Cell Viability Assay Kit (Daeil Lab Co, Seoul, Korea). The formazan dye was analyzed spectrophotometrically by measuring the absorbance at 450 nm using a Chameleon multi-label plate reader (Hidex Personal Life Science, Hidex Oy, Finland).

[Real-Time RT-PCR]

Total RNA was isolated using a Trizol reagent (Invitrogen, Carlsbad, Calif., USA) according to the manufacturer's instructions. CDNA was synthesized with 2.5 μg of total RNA using ImProm-II™ Reverse Transcription system (Promega, Madison, Wis., USA). For the expression level of each gene, PCR was amplified with the synthesized cDNA using DNA Engine Opticon 1 (MJResearch, Waltham, Mass., USA). For the detection of fluorescence during the PCR amplification, SYBR Premix Ex Taq (Takara Bio, Otsu, Japan) was used. The total volume was 10 μl, to which 1 μl of cDNA/control and a primer specific to each gene were added to perform the PCR amplification. The primers used were as follows:

```
MMP-1
Forward:
CTG AAG GTG ATG AAG CAG CC

Reverse:
AGT CCA AGA GAA TGG CCG AG

MMP-2
Forward:
GAT ACC CCT TTG ACG GTA AGG A
```

```
-continued
Reverse:
CCT TCT CCC AAG GTC CAT AGC

MMP-3
Forward:
ATT CCA TGG AGC CAG GCT TTC

Reverse:
CAT TTG GGT CAA ACT CCA ACT GTG

GAPDH
Forward:
CGG AGT CAA CGG ATT TGG TCG TAT

Reverse:
AGC CTT CTC CAT GGT GGT GAA GAC
```

The conditions for carrying out the PCR amplification reaction were as follows:
(1) Denaturation at 95° C. for 10 minutes
(2) 40 cycles: denaturation (95° C., 1 sec), annealing (60° C., 5 sec), extension (72° C., 25 sec).

[Western Blotting Analysis]

The total protein extracts from the samples were dissolved in lysis buffer (50 mM Tris (pH 7.4), 150 mM NaCl, 1 mM EGTA, 1% NP-40, 0.25% sodium deoxycholate, 1 mM PMSF, and phosphatase inhibitor mixture (Sigma, St. Louis, Mo., USA) and then boiled for 5 minutes. The dissolved proteins were quantitated using Bio-Rad Protein Assay Dye Reagent Concentrate (Bio-Rad Laboratories, Hercules, Calif., USA) and then separated by SDS-PAGE and transferred to a polyvinylidene difluoride (PVDF) membrane (Amersham Pharmacia Biotech, Piscataway, N.J., USA). Membranes were reacted with specific primary antibodies overnight at 4° C., and protein bands were then visualized using secondary antibodies coupled with horseradish peroxidase (HRP) and a chemiluminescence detection kit (Amersham Pharmacia Biotech). Each of the primary antibodies used was as follows: MMP-1 (Chemicon, Bedford, Mass., USA), MMP-2 (Chemicon, Bedford, Mass., USA), MMP-3 (Epitomics, Burlingame, Calif., USA), phosphor c-Jun N-terminal kinase (pJNK), JNK, phospho extracellular signal-regulated kinase (pErk) and Erk (all commercially available from Cell Signaling Technology, Beverly, Mass., USA).

[Confocal Microscopy]

HDF cells were cultured on a coverslip at 5×104/well and then treated with pheophorbide a for 2 hours without exposure to lights at 37° C. The cells were fixed with 4% paraformaldehyde in PBS. The fluorescence of pheophorbide a was visualized using a FV1000 confocal microscope (Olympus, Tokyo, Japan) at 440 nm excitation wavelength and 655 nm emission wavelength. The intracellular uptake of pheophorbide a was determined by fluorescence intensity.

[Experimental Animal]

Premature female SKH-1 hairless mice were purchased from Charles River Laboratories (Wilmington, Mass.) and adapted for one week. The mice were housed in air-conditioned rooms in a 12-hour light/12-hour dark cycle to allow them to eat water and food freely. The room temperature was maintained at 23±3° C. and under humidity at 55±15%. All experiments were approved by the Animal Care and Use Committee at Gwangju Institute of Science and Technology.

[Oral Administration of Test Material]

After the adaptation period, mice were divided into 4 groups of 6 mice per each group. Each of the groups was as follows:
(a) Negative control group
(b) Positive control group with only UV irradiation
(c) Group of receiving 5 mg/kg daily chlorophyll a with UV irradiation
(d) Group of receiving 5 mg/kg pheophorbide a daily with UV irradiation Chlorophyll a (Ca, Sigma-Aldrich, St Louis, Mo., USA) or pheophorbide a (Pa, Frontier Scientific, Logan, Utah, USA) was dissolved in a solution of 40% polyethylene glycol 400 (Sigma-Aldrich, St Louis, Mo., USA), respectively. As a control, vehicle was prepared with only 40% polyethylene glycol 400 solution and administered to mice in the negative control and positive control groups. The administration of test materials was made immediately after UV irradiation.

[Wrinkle Evaluation of Dorsal Skin]

A digital camera (Sony Cybershot DSC-W570, 5× optical zoom, 16.1 megapixels, Sony Corporation, Tokyo, Japan) was used to obtain a clinical image of the dorsal skin after continuous exposure to low dose UV. The enlarged wrinkles were obtained using DermLite®IIHybridM (3Gen, LLC, San Juan Capistrano, Calif., USA) attached to the digital camera. The wrinkles of the dorsal skin of the mice were graded according to the method described by Bissett et al. [20]. The grades were as follows:
Grade 0—no thick wrinkles;
Grade 1—a few shallow thick wrinkles;
Grade 2—some thick wrinkles;
Grade 3—multiple deep thick wrinkles.

A negatively imprinted replica was used to analyze the wrinkles of the skin, which is described by Ryu et al. [21]. That is, a semi-fluidic silicone polymer was mixed with a catalyst (Imprint II Garant™ Light Body, 3M) and then applied to a dorsal skin sufficiently to penetrate into the wrinkles beyond a contour. This replica was analyzed under standard illumination with an incident angle where the replica was formed and set to produce a reflective shadow proportional to the height of the wrinkles. The captured images were analyzed from a shadow region in the images using image analysis software (ImageJ software, NIH Image, National Institutes of Health, Bethesda, Md., USA; online at: http://rsb.info.nih.gov/ij/).

[Histological Examination]

Tissue samples taken from the dorsal skin of UV-irradiated mice were fixed in 4% paraformaldehyde and then included in paraffin. Thin sections with a thickness of 4 μm were stained with hematoxylin and eosin solution. To visualize collagen deposition, the sections were stained with Accustain trichrome stain (Sigma-Aldrich, St. Louis, Mo., USA). The epidermal thickness from a junction of the granular keratocytes to a junction of the dermis-epidermis was measured using an i-Solution DT image acquisition and analysis program (IMT 20 i-solution, Vancouver, Canada) and a Leica microscope (Leica, Wetzlar, Germany). To assess the thickness of the epidermis, any of the ten sites on the slide were measured. In high performance field, inflammatory cells from epidermis to subcutaneous fat layer were calculated.

[Immunohistochemistry]

Immunohistochemical staining for MMP-1 (Chemicon International, Temecula, Calif., USA), ICAM-1 (Santa Cruz Biotech, Santa Cruz, Calif., USA) and Type 1 Collagen (Santa Cruz Biotechnology, Santa Cruz, Calif., USA) was performed using a paraffin tissue section with 5 μm thickness. Paraffin was removed from the slides using xylene and alcohol, and hydrated. The sections were incubated in 3% H2O2 to remove endogenous peroxidase and then incubated with 3% bovine serum albumin to block non-specific antibody binding sites. Mouse anti-human MMP-1 monoclonal antibodies (1:100), goat anti-human type 1 collagen polyclonal antibodies (1:100) and mouse anti-human ICAM-1 monoclonal antibodies (1:100) were prepared, respectively, to detect MMP-1, type 1 collagen and ICAM-1. Then, the avidin-biotin-peroxidase complex method was applied using DAKO LSAB+system-HRPkit (DAKO Corporation, Carpinteria, Calif., USA) to visualize a specific target of each antibody. Hematoxylin was used as a control stain.

[Statistical Analysis]

Each in vitro experiment was performed in triplicate and all data were expressed as mean±standard deviation. Significant differences between the groups were analyzed by Student T test and ANOVA. P-value <0.05 was considered statistically significant.

[Experiment Results]

The clinical scores of wrinkles were improved in the group administered with pheophorbide a or chlorophyll a Skin wrinkles were evaluated in hairless mice repeatedly irradiated with UV for 8 weeks. Skin characteristics of wrinkles and negative replica images in the back of the mice were taken with a digital camera and analyzed with image analysis software (FIG. 1). When the dorsal skin of mice was repeatedly exposed to UVB over a long period of time, wrinkles and skin roughness, which are typical characteristics of photoaging, were induced. In the case of the mice administered with pheophorbide a or chlorophyll a immediately after UV irradiation, the thickness of wrinkles was remarkably reduced and fine wrinkles were shown, compared with the control group. In addition, two skilled practitioners identified visual wrinkle ratings for clinical images, indicating that wrinkles grades were lower in the group administered with either pheophorbide a or chlorophyll a. In the replicated images, the group administered with either pheophorbide a or chlorophyll a showed a decrease in the wrinkle area compared to the control group.

Figure 2A:
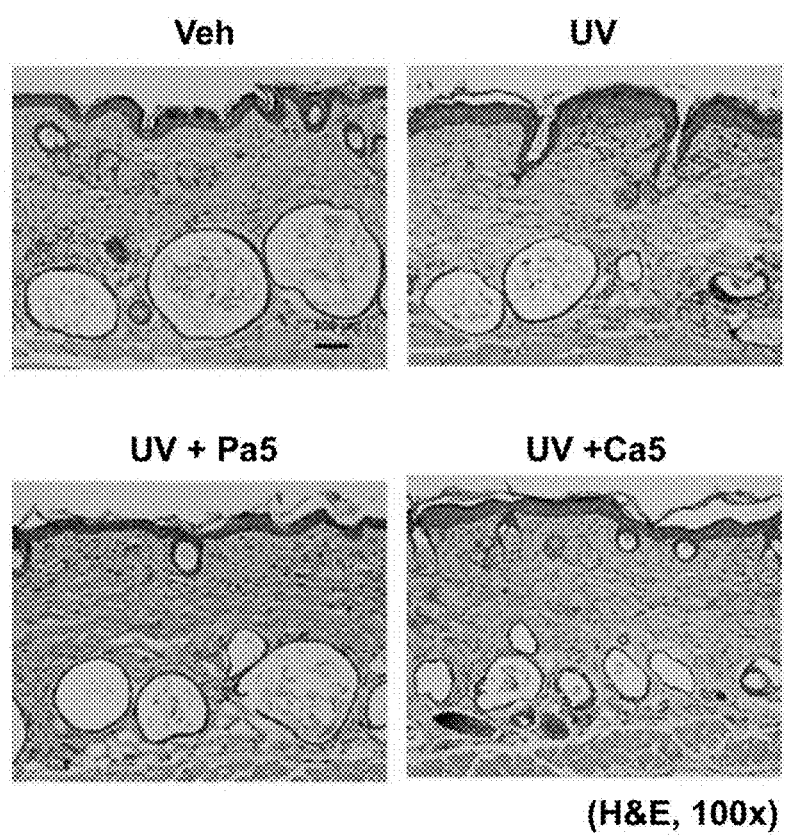
Figure 2B:
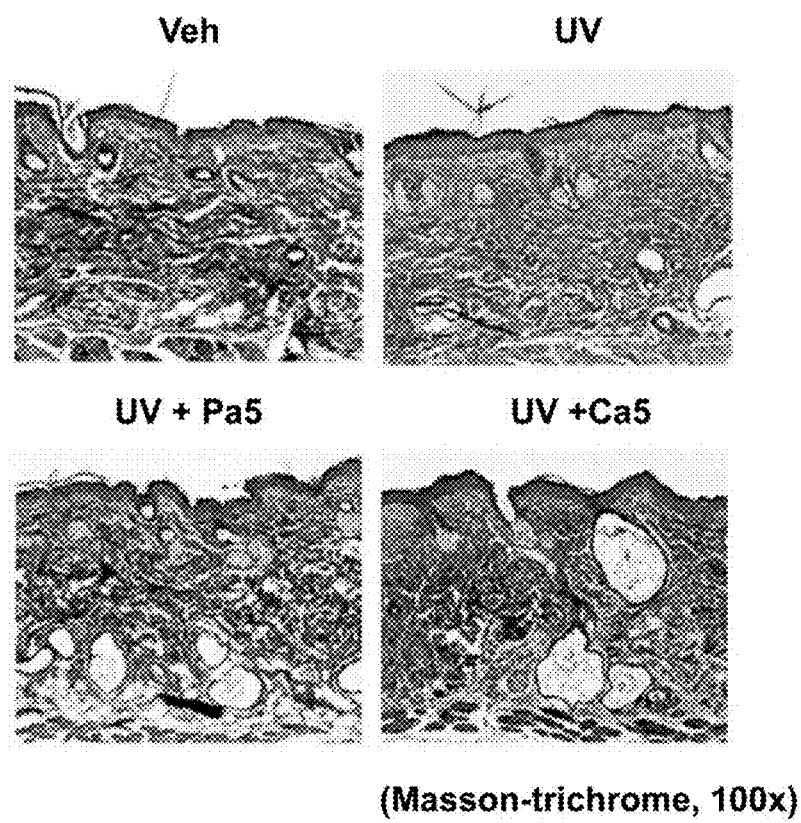
Figure 2C:
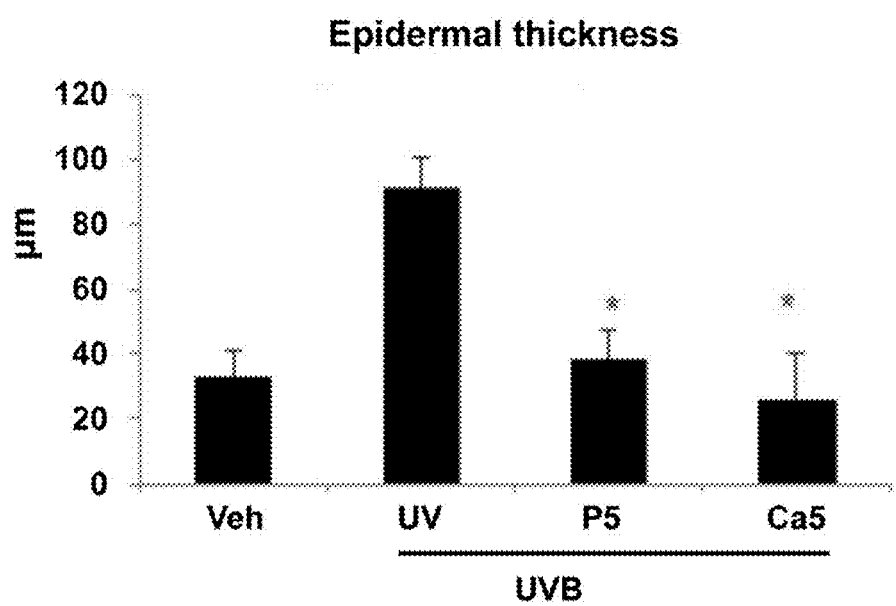
FIG. 2c is a graph showing that the thickness of epidermis was decreased in a mouse administered with pheophorbide a or chlorophyll a, compared with a mouse irradiated only with UV.

Histopathology of dorsal skin was improved in mice treated with pheophorbide a or chlorophyll a To investigate the effect of pheophorbide a or chlorophyll a on an inflammatory reaction induced by UV irradiation, the dorsal skin of UV-irradiated mice was sectioned and stained with H & E (FIG. 2). In the group administered with pheophorbide a or chlorophyll a, it was confirmed that the infiltration of inflammatory cells in the epidermis and upper dermis was reduced compared with the control group.

Thickening of the epidermis means that there was an inflammatory reaction induced by UV irradiation, where the thickness of the epidermis was evaluated by Masson-trichrome staining. In the UV irradiated group, the epidermal thickness was increased compared to the control group treated only with vehicle. A decrease in thickness in the group administered with either pheophorbide a or chlorophyll a indicates that the level of inflammation has decreased. It was also observed that in the group administered with either pheophorbide a or chlorophyll a less collagen breakdown occurred in the dermis than in the control group. That is, in the UV-only-irradiated group, fine collagen bundles were observed in the epidermis. Further, it was observed that degenerative hyalinized materials were deposited and spread along the dermal-epidermal junction and the upper dermis. On the other hand, in the group administered with either pheophorbide a or chlorophyll a, it was observed that the degenerative materials in the thick dermal collagen bundle and upper dermis were reduced compared to the control group.

Figure 3A:
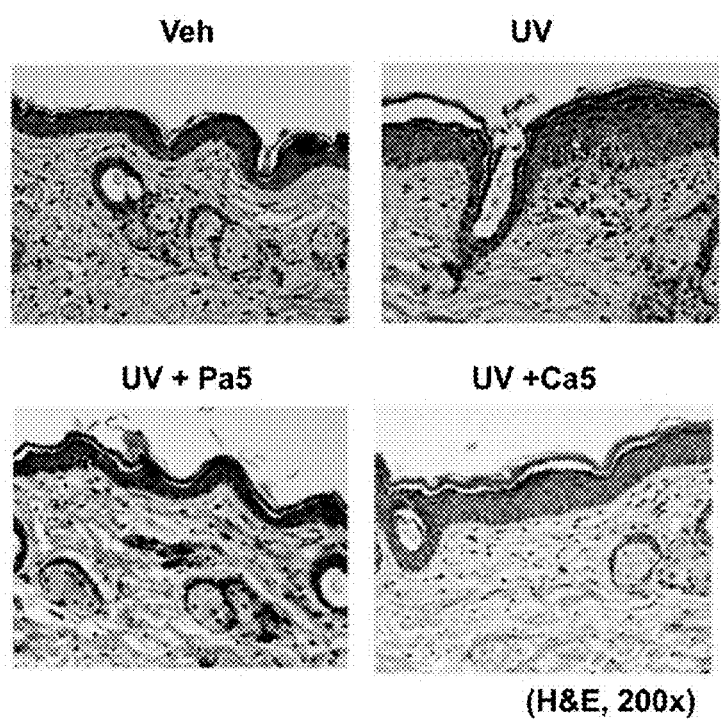
Figure 3B:
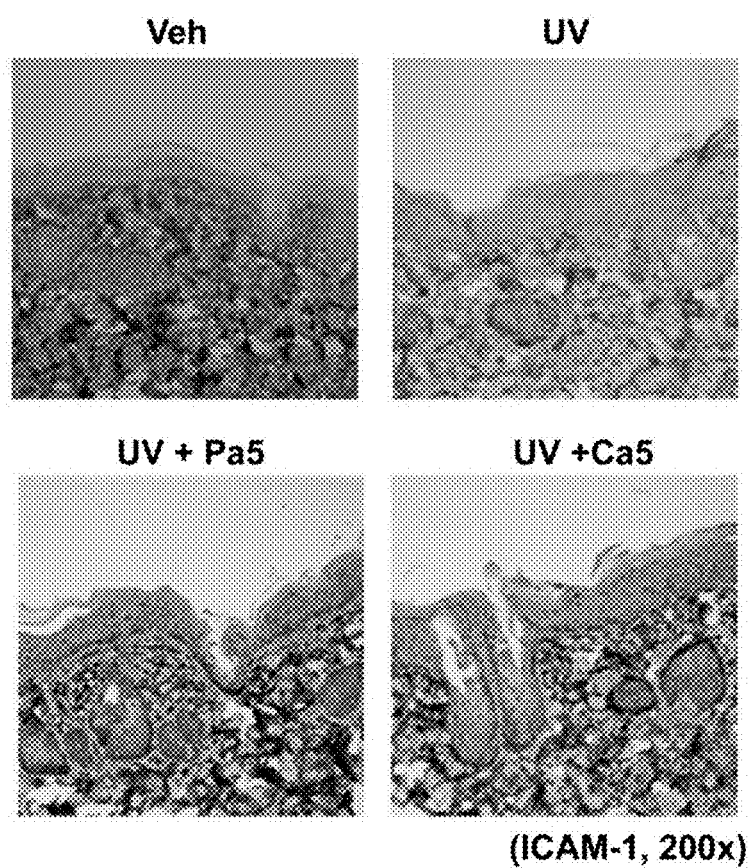
FIG. 3b is a photograph showing that ICAM-1 was significantly highly expressed in the dermal upper part and in the epidermis of an UV-irradiated mouse, compared to those of a vehicle-only administered mouse. Expression of ICAM-1 was decreased in the mouse administered with pheophorbide a or chlorophyll a, compared to the UV-irradiated mouse.
Figure 3C:
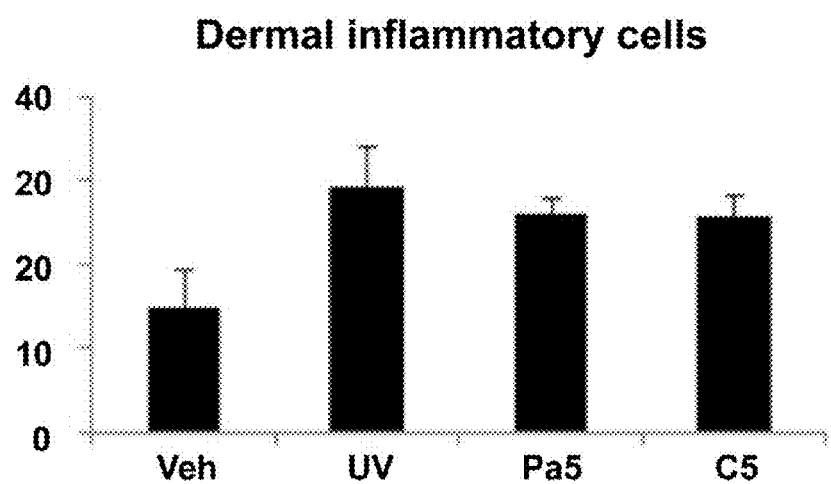
FIG. 3c is a graph showing that the infiltration of inflammatory cells was reduced in a mouse administered with pheophorbide a or chlorophyll a as compared with that of UV-irradiated mouse, in view of the infiltration of inflammatory cells with a fluorescence microscope.

The expression of intercellular adhesion molecule-1 (ICAM-1) was reduced in the pheophorbide a or chlorophyll a administered group compared to the UV-only-irradiated control group Intercellular adhesion molecule-1 (ICAM-1) is a cell surface adhesion molecule that mediates leukocyte interactions and aggregates inflammatory cells. It is known that UV irradiation induces ICAM-1 in keratinocytes, and ICAM-1 is expressed at a high level in the cell membrane of inflammatory sites where infiltration of inflammatory cells occurs [22]. Immunohistochemical staining for ICAM-1 revealed that the expression of ICAM-1 was increased in the epidermis and upper dermis of the UV-treated group compared to the vehicle-treated group (FIG. 3). This seems to be due to the infiltration of inflammatory cells in the upper dermis. In the group administered with either pheophorbide a or chlorophyll a, the level of ICAM-1 expression was decreased in the epidermis and upper dermis compared with the UV-only-irradiated group.

Treatment with pheophorbide a after UV irradiation in human dermal fibroblast (hDF) reduces the production of matrix metalloproteinase (MMP)

Figure 4A:
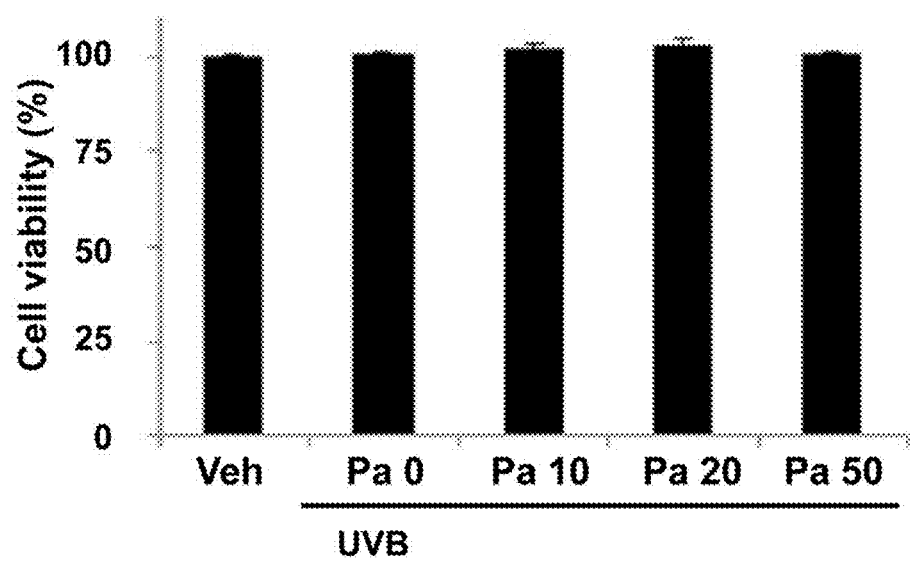

In order to evaluate the effect of pheophorbide a on MMP production, hDF cells were cultured up to 80% of the culture dish and then irradiated with UV (20 mJ/cm2) and treated with various concentrations (0, 10, 20, 50 μM) of pheophorbide a. Cells were cultured for 72 hours in the absence of light, and cytotoxicity assays were then performed. Cell viability was not affected by UV irradiation and test material treatment (FIG. 4a).

Figure 4B:
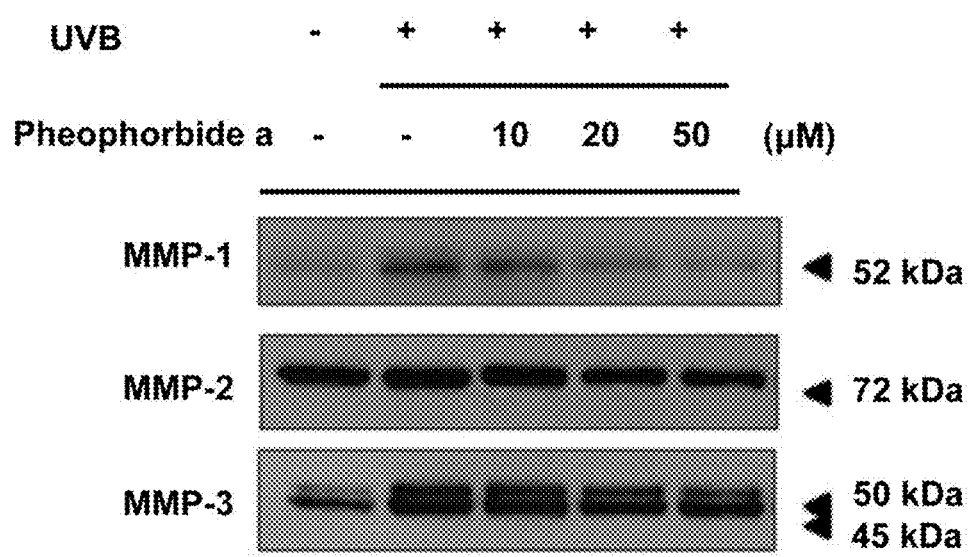
Figure 4C:
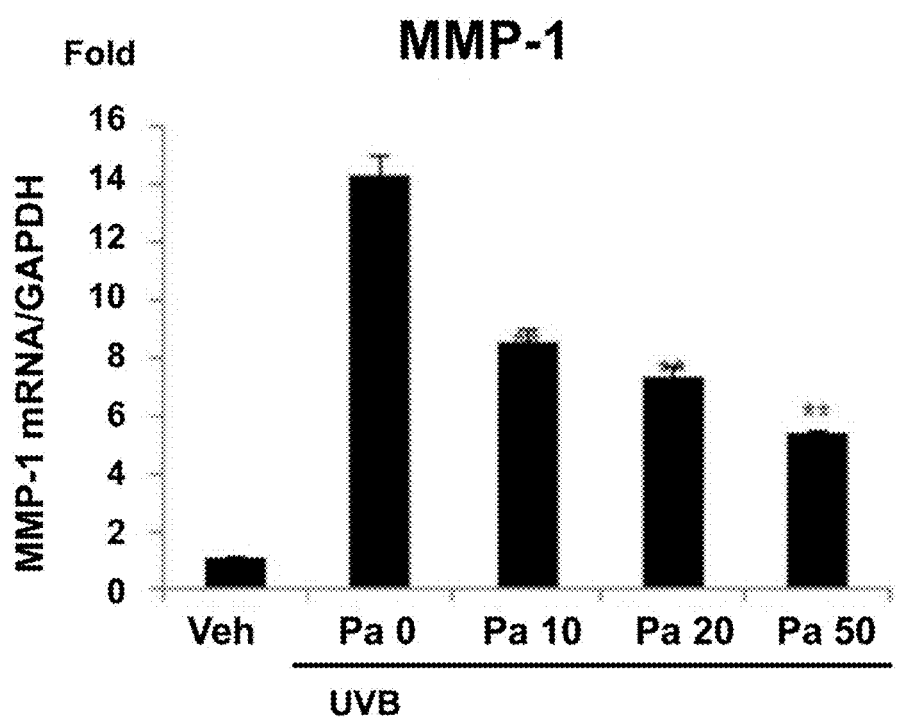
Figure 4D:
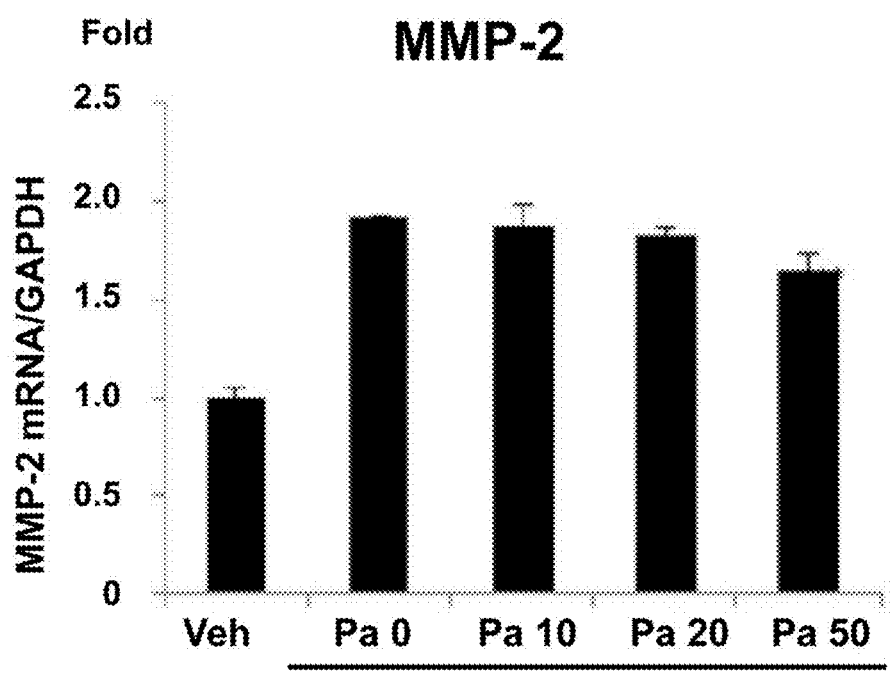
Figure 4E:
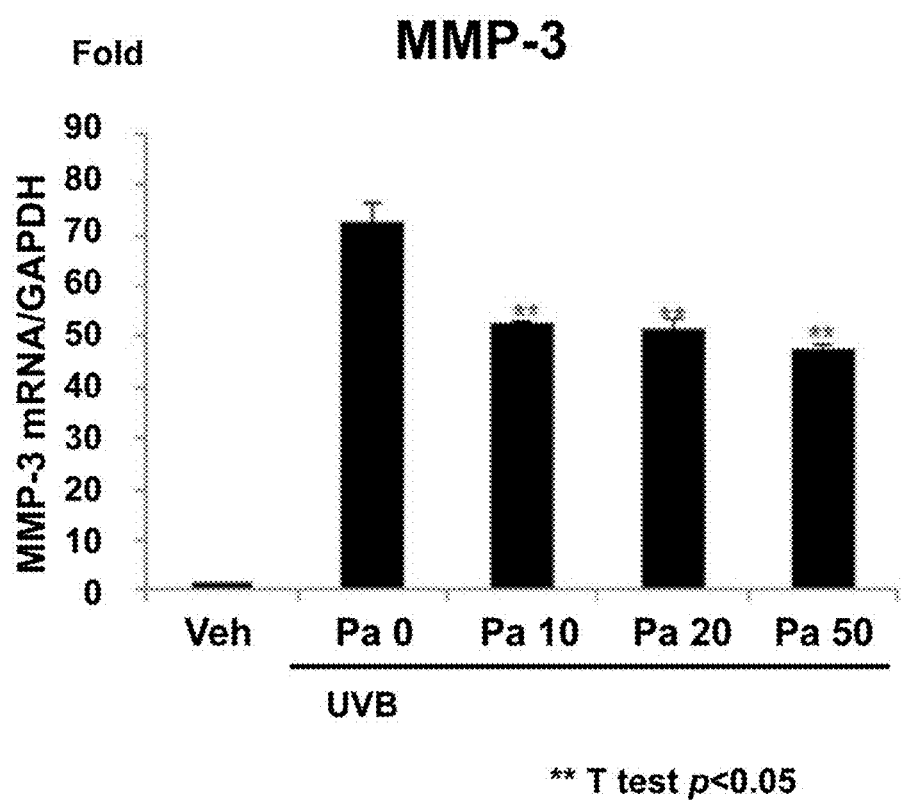

In addition, UV was irradiated, the test materials were treated, cultured for 24 hours, and then the mRNA level of MMPs was analyzed using a real time RT PCR method. GAPDH gene was used as an internal control and the amount of MMP-1 relative to GAPDH was expressed in bars (FIGS. 4c-e). MMP-1/GAPDH mRNA levels were increased 14-fold when irradiated with UV only. When treated with pheophorbide a, a significant decrease in MMP-1 and MMP-3 levels were found. MMP-2 mRNA levels were hardly affected by UV irradiation.

Western blotting analysis was performed to confirm the expression level of MMP proteins. Analysis of primary antibodies for MMP-1, MMP-2 and MMP-3 revealed that MMP-1 and MMP-3 decreased in proportion to the amount treated with pheophorbide a (FIG. 4b). In conclusion, protein levels were consistent with mRNA expression levels.

Figure 5A:
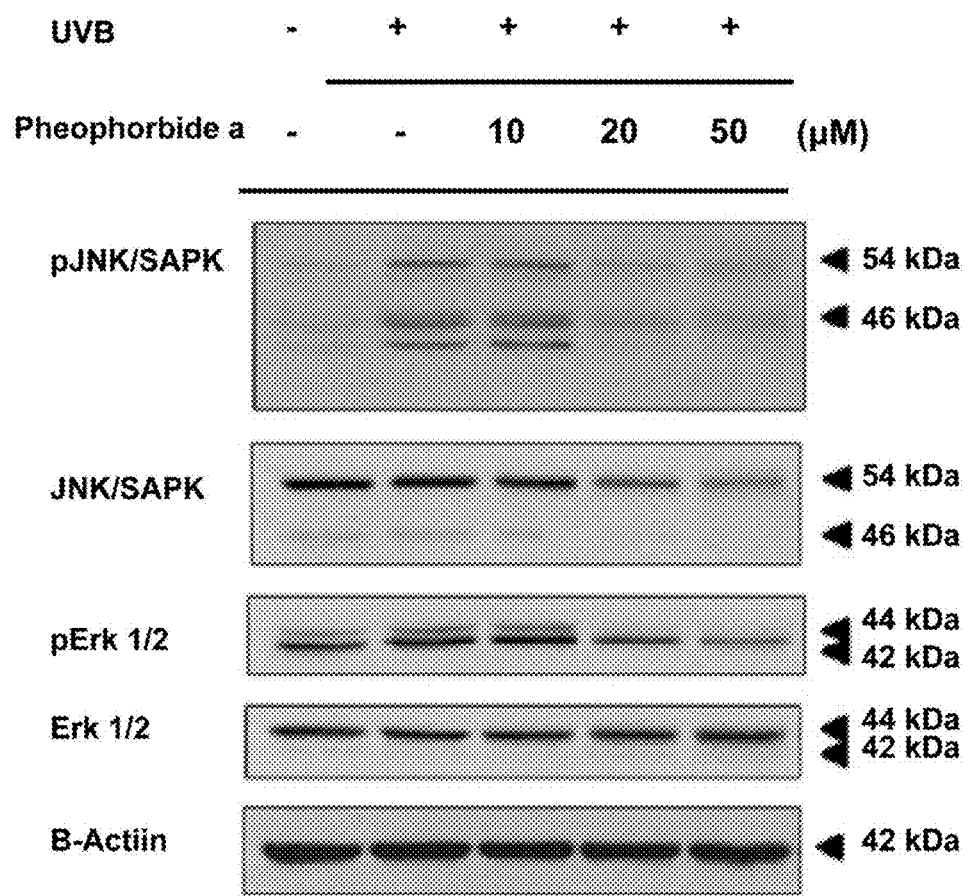

In human skin fibroblasts (hDF), pheophorbide a inhibits phosphorylation of mitogen-activated protein kinase (MAPK) induced by UV irradiation MMPK is known to be involved in the production of MMP induced by UV irradiation. It was intended to determine the effect of pheophorbide a on the phosphorylation of MAPK by UV irradiation. To this end, UV-irradiated hDF cells were treated with pheophorbide a and cultured for 2 hours in the absence of light, followed by Western blotting analysis (FIG. 5a). To determine the expression levels of phosphorylated c-Jun N-terminal kinase (pJNK), JNK, phosphorylated extracellular signal-5 regulated kinase (pErk) and Erk proteins, the primary antibodies for each protein were used. Western blotting analysis showed that expression levels of phosphorylated JNK and phosphorylated Erk decreased in cells treated with 20 μM and 50 μM pheophorbide a. In addition, the basal JNK protein levels decreased in proportion to the amount of pheophorbide a.

Figure 5B:
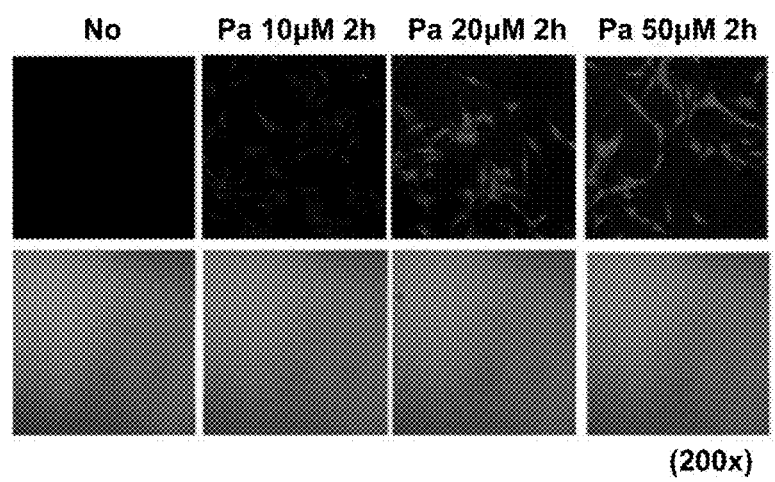
FIG. 5b is a photograph showing that hFD cells were treated with pheophorbide a and observed with a confocal microscope for 2 hours to find that pheophorbide a was located in cytoplasm in proportion to its concentration.

The absorptions of pheophorbide a in hDF cells for 2 hours were visualized using a confocal microscope image (FIG. 5b). Western blotting analysis of MAPK showed that MAPK phosphorylation inhibition was not as much as 20 μM and 50 μM when treated with 10 μM pheophorbide a for 2 hours after UV irradiation, which was probably due to the fact that cell uptake did not occur well at 10 μM pheophorbide a compared to 20 μM and 50 μM pheophorbide a.

REFERENCES

[1] Jenkins, G., Molecular mechanism of skin aging. Mech. Ageing. Dev. 2002, 123, 801-810.

[2] Kim, H H., Lee, M J., Lee S R., Kim K H., et al., Augmentation of UV-induced skin wrinkling by infrared irradiation in hairless mice. Mech. Ageing. Dev. 2005, 126, 1170-1177.

[3] Gelse, K., Pschl, E., Aigner, T., Collagens—structure, function, and biosynthesis. Adv. Drug. Deliv. Rev. 2003, 55, 1531-1546.

[4] Ferruzzi, M G., Failla, M L., Schwartz, S J., Assessment of degradation and intestinal cell uptake of carotenoids and chlorophyll derivatives from spinach puree using an in vitro digestion and Caco-2 human cell model. J. Agric. Food. Chem. 2001, 49, 2082-2089.

[5] Schoefs, B., Chlorophyll and carotenoid analysis in food products. Properties of the pigments and methods of analysis. Trends. Food. Sci. Technol. 2002, 13, 361-371.

[6] Czerpak, R., Pietryczuk, A., Therapeutic, cosmetic and dietary significance of some algae. Postepy. Fitoterapii. 2009, 10, 168-174.

[7] Negishi, T., Rai, H., Hayatsu, H., Antigenotoxic activity of natural chlorophylls. Mutat. Res. 1997, 376, 97-100.

[8] Nakamura, Y., Murakami, A., Koshimizu, K., Ohigashi, H., Identification of pheophorbide a and its related compounds in the leaves of *Neptunia oleracea*. Biosci. Biotechnol. Biochem. 1996, 60, 1028-1030.

[9] Nakamura, Y., Murakami, A., Koshimizu, K., Ohigashi, H., Inhibitory effect of pheophorbide a, a chlorophyll related compound, on skin tumor promotion in ICR mice. Cancer. Lett. 1996, 108, 247-255.

[10] Harttig, U., Bailey, G. S., Chemoprevention by natural chlorophylls in vivo: inhibition of dibenzo[a, I]pyrene—DNA adducts in rainbow trout liver. Carcinogenesis 1998, 19, 1323-1326.

[11] Dougherty, T. J., Gomer, C. J., Henderson, B. W., et al., Photodynamic therapy. J. Natl. Cancer. Inst. 1998, 90, 889-905.

[12] Endo, H., Hosoya, H., Koyama, T., Ichioka, M., Isolation of 10-hydroxypheophorbide a as a photosensitizing pigment from alcohol-treated *chlorella* cells. Agric. Biol. Chem. 1982, 46, 2183-2193.

[13] Fujishima, I., Sakai, T., Tanaka, T., Ryu, H., et al., Photodynamic Therapy Using Pheophorbide a and Nd:YAG Laser. Neurol. Med. Chir. (Tokyo). 1991, 31, 257-263.

[14] Matsuura, E., Aoki, K., Hirano, R., Yamada, K., Kawahara, H., Photodynamic action of salted Takana or pheophorbide a in the salted Takana on erythrocyte of rats. Eiy.o To. Shokuryo. 1977, 30, 307-311 (in Japanese).

[15] Heaton J. W., Marangoni A. G., Chlorophyll degradation in processed foods and senescent plant tissues. Trends. Food. Sci. Tech. 1996, 7, 8-15

[16] Heinrich, M., Bork, P. M., Schmitz, M. L., Rimpler, H., et al., Pheophorbide A from *Solanum diflorum* interferes with NF-B activation. Planta. Med. 2001, 67, 156-157.

[17] Subramoniam, A., Asha, V. V., Nair, S. A., Sasidharan, S. P., et al., Chlorophyll revisited: Anti-inflammatory activities of chlorophyll a and inhibition of expression of TNF-gene by the same. Inflammation. 2012, 35, 959-966.

[18] Islam, M. N., Ishita, I. J., Jin, S. E., Choi, R. J., et al., Anti-inflammatory activity of edible brown alga *Saccharina japonica* and its constituents pheophorbide a and pheophytin a in LPS-stimulated RAW 264.7 macrophage cells. Food. Chem. Toxicol. 2013, 55, 541-548.

[19] Lee, J. Y., Zhao, L., Youn, H. S., Weatherill, A. R., et al., Saturated fatty acid activates but polyunsaturated fatty acid inhibits Toll-like receptor 2 dimerized with Toll-like receptor 6 or 1. J. Biol. Chem. 2004, 279, 16971-16979.

[20] Bissett, D. L., Hannon, D. P., Orr, T. V., An animal model of solar-aged skin: histological, physical, and visible changes in UV-irradiated hairless mouse skin. Photochem. Photobiol. 1987, 46, 367-378.

[21] Ryu, J. S., Park, S. G., Kwak, T. J., Chang, M. Y., et al., Improving lip wrinkles: lipstick related image analysis. Skin. Res. Technol. 2005, 11, 157-164.

[22] Krutmann, J., Grewe, M., Involvement of cytokines, DNA damage, and reactive oxygen intermediates in ultraviolet radiation-induced modulation of intercellular adhesion molecule-1 expression. J. Invest. Dermatol. 1995, 105 (1 Suppl), 67S-70S.

[23] Fisher, G. J., Wang, Z. Q., Datta, S. C., Varani, J., et al., Pathophysiology of premature skin aging induced by ultraviolet light. N. Engl. J. Med. 1997, 337, 1419-1428.

[24] Lee, Y. M., Li, W. H., Kim, Y. K., Kim, K. H., Chung, J. H., Heat-induced MMP-1 expression is mediated by TRPV1 through PKC alpha signaling in HaCaT cells. Exp. Dermatol. 2008, 17, 864870.

[25] Saarialho-Kere, U. K., Crouch, E. C., Parks, W. C., Matrix metalloproteinase matrilysin is constitutively expressed in adult human exocrine epithelium. J. Invest. Dermatol. 1995,105, 190196.

[26] Ropke, C. D., Sawada, T. C., da Silva, V. V., Michalany, N. S., de Moraes Barros, S. B., Photoprotective effect of *Pothomorphe umbellata* root extract against ultraviolet radiation induced chronic skin damage in the hairless mouse. Clin. Exp. Dermatol. 2005, 30, 272-276.

[27] Cho, H. S., Lee, M. H., Lee, J. W., No, K. O., et al., Anti-wrinkling effects of the mixture of vitamin C, vitamin E, pycnogenol and evening primrose oil, and molecular mechanisms on hairless mouse skin caused by chronic ultraviolet B irradiation. Photodermatol. Photoimmunol. Photomed. 2007, 23, 155-162.

[28] Kang, T. H., Park, H. M., Kim, Y. B., Kim, H., et al., Effects of red *ginseng* extract on UVB irradiation-induced skin aging in hairless mice. J. Ethnopharmacol. 2009, 123, 446-451.

[29] Bae, J. Y., Choi, J. S., Kang, S. W., Lee, Y. J., et al., Dietary compound ellagic acid alleviates skin wrinkle and inflammation induced by UV-B irradiation. Exp. Dermatol. 2010, 19, 182-190.

[30] Vayalil, P. K., Mittal, A., Hara, Y., Elmets, C. A., Katiyar, S. K., Green tea polyphenols prevent ultraviolet light-induced oxidative damage and matrix metalloproteinases expression in mouse skin. J. Invest. Dermatol. 2004, 122, 1480-1487.

[31] Ferruzzi, M. G., Blakeslee, J., Digestion, absorption, and cancer preventative activity of dietary chlorophyll derivatives. Nutr. Res. 2007, 27, 1-12.

[32] Muthusamy, V., Piva, T. J., The UV response of the skin: a review of the MAPK, NFB and TNF signal transduction pathways. Arch. Dermatol. Res. 2010, 302, 5-17.

[33] Yarr, M., in: Wolff K (Ed.), Fitzpatrick's Dermatology in General Medicine, 7th edn—Aging of Skin, McGraw-Hill, New York, 2008, pp. 963-973.

[34] Kundu, J. K., Chun, K. S., Kim, S. O., Surh, Y. J., Resveratrol inhibits phorbol ester-induced cyclooxygenase-2 expression in mouse skin: MAPKs and AP-1 as potential molecular targets. Biofactors 2004, 21, 33-39.

[35] Sharma, S. D., Meeran, S. M., Katiyar, S. K., Dietary grape seed proanthocyanidins inhibit UVBinduced oxidative stress and activation of mitogen-activated protein kinases and nuclear factor kappa B signaling in in vivo SKH-1 hairless mice. Mol. Cancer Ther. 2007, 6, 995-1005.

[36] Cui, G., Qin, X., Zhang, Y., Gong, Z., et al., Berberine differentially modulates the activities of ERK, p38 MAPK, and JNK to suppress th17 and th1 t cell differentiation in type 1 diabetic mice. J. Biol. Chem. 2009, 284, 28420-28429.

[37] Wu, L. C., Lin, Y. Y., Yang, S. Y., Weng, Y. T., Tsai, Y. T., Antimelanogenic effect of c-phycocyanin through modulation of tyrosinase expression by upregulation of ERK and downregulation of p38 MAPK signaling pathways. J. Biomed. Sci. 2011, 18, 74.

The invention claimed is:

1. A method for treating skin damage caused by ultraviolet lights, or for ameliorating or treating sunburn, comprising administering to a subject a composition comprising chlorophyll a or pheophorbide a as an active ingredient.

2. The method according to claim 1, wherein the chlorophyll a or pheophorbide a is administered orally.

3. The method according to claim 1, wherein the active ingredient inhibits MMP-1 (matrix metalloproteinase-1) and MMP-3.

4. The method according to claim 1, wherein the ameliorating or treating skin damage comprises improving skin wrinkles, or relieving skin inflammations.

5. The method according to claim 1, wherein the skin damage caused by ultraviolet lights is skin wrinkles.

6. The method according to claim 1, wherein the active ingredient has anti-inflammatory activity.

7. The method according to claim 1, wherein the composition is a cosmetic composition.

8. The method according to claim 1, wherein the composition is a pharmaceutical composition.

9. The method according to claim 1, wherein the composition is a food composition.

* * * * *